United States Patent [19]
Fucci et al.

[11] Patent Number: 5,601,586
[45] Date of Patent: Feb. 11, 1997

[54] VARIABLE ANGLE ROTATING SHAVER

[75] Inventors: Joseph Fucci, Port Richey; Fred B. Dinger, III, Belleair; A. Frank Trott, Largo; Kenneth M. Adams, Pinellas Park; William F. Mazurek, Palm Harbor, all of Fla.

[73] Assignee: Linvatec Corporation, Largo, Fla.

[21] Appl. No.: 373,165

[22] Filed: Jan. 17, 1995

Related U.S. Application Data

[62] Division of Ser. No. 265,558, Jun. 24, 1994, Pat. No. 5,411,514, which is a continuation of Ser. No. 26,613, Mar. 5, 1993, abandoned, which is a continuation-in-part of Ser. No. 954,099, Sep. 30, 1992, abandoned.

[51] Int. Cl.⁶ .................................................. A61B 17/32
[52] U.S. Cl. .............................................. 606/180; 138/122
[58] Field of Search ............................. 138/122; 604/22; 606/159, 170–171, 180

[56] References Cited

U.S. PATENT DOCUMENTS

| | | |
|---|---|---|
| 4,071,029 | 1/1978 | Richmond et al. . |
| 4,466,429 | 8/1984 | Loscher et al. . |
| 4,576,772 | 3/1986 | Carpenter . |
| 4,646,738 | 3/1987 | Trott . |
| 4,858,897 | 8/1989 | Irifune . |
| 4,923,441 | 5/1990 | Shuler . |
| 4,998,527 | 3/1991 | Meyer . |
| 5,061,238 | 10/1991 | Shuler . |
| 5,074,841 | 12/1991 | Ademovic et al. . |
| 5,152,744 | 10/1992 | Krause et al. . |

FOREIGN PATENT DOCUMENTS

WO92/08416  5/1992  WIPO .

*Primary Examiner*—Guy V. Tucker
*Assistant Examiner*—Nancy Connolly Mulcare
*Attorney, Agent, or Firm*—Gene Warzecha

[57] ABSTRACT

A surgical cutting instrument having an elongated rotatable inner member provided with a cutting edge at its distal tip, the inner member adapted to rotate within an elongated outer tube having a window adjacent its distal end adapted to cooperate with the cutting edge of the inner member. The outer tube is provided with a portion thereof adjacent its distal end which enables the distal tip of the outer tube to be bent at an angle relative to the proximal portion of the outer tube. The outer tube may be bent by a user into a selected angular position with the aid of a tool calibrated in a plurality of discrete positions. The tool is adapted to enable the outer tube to be rotated to any selected position prior to being bent so that the window at the distal tip of the outer tube may be caused to face in any desired direction relative to the bend in the outer tube.

9 Claims, 8 Drawing Sheets

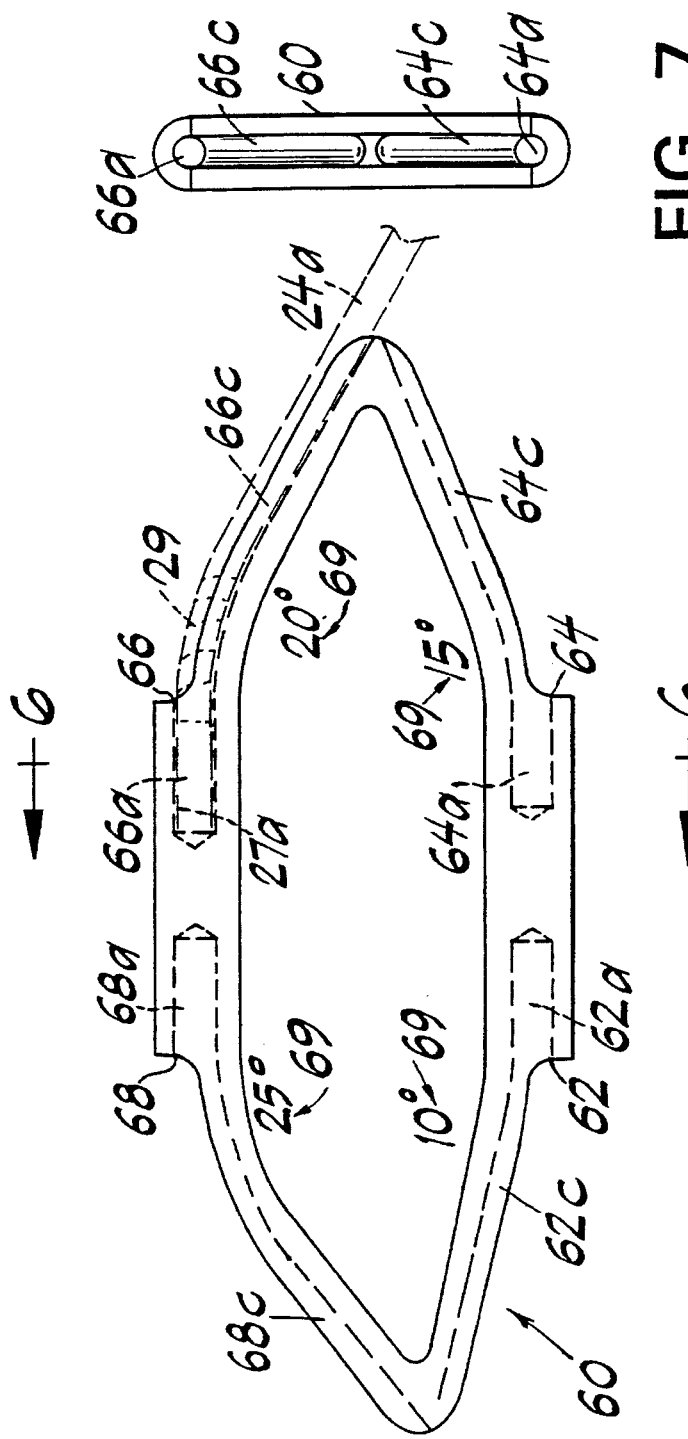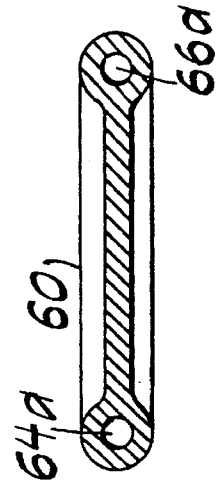

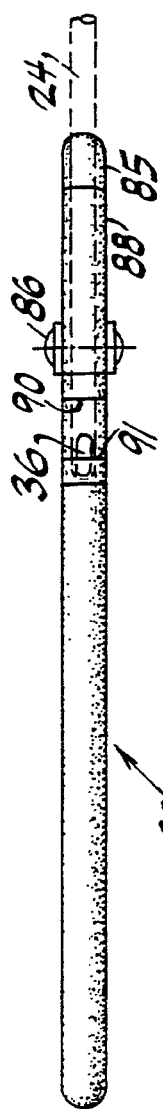
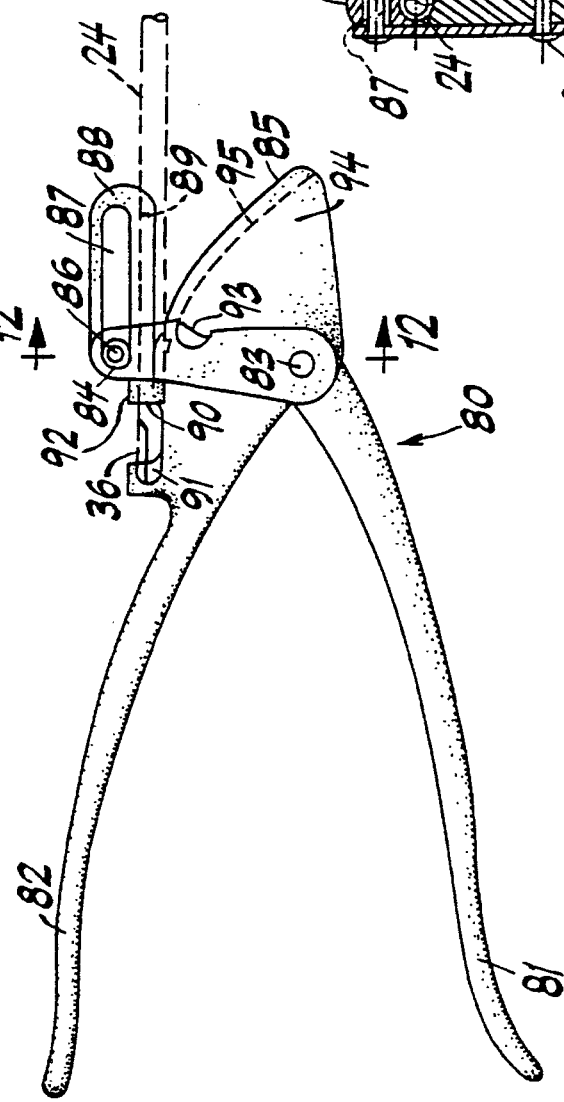
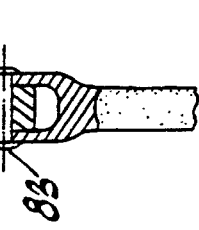
FIG. 11
FIG. 10
FIG. 12

VARIABLE ANGLE ROTATING SHAVER

This is a divisional application of application Ser. No. 08/265,558 filed Jun. 24, 1994, now U.S. Pat. No. 5,411,514 which is a continuation of application Ser. No. 08/026,613 filed Mar. 5, 1993, now abandoned, which is a continuation-in-part of application Ser. No. 07/954,099, filed Sep. 30, 1992, now abandoned.

BACKGROUND OF THE INVENTION

1. Field of the Invention

The present invention pertains to surgical cutting instruments and, more particularly, to surgical cutting instruments having an elongated inner cutting member rotating about its axis within an elongated outer tubular member having a cutting window at its distal end which cooperates with the inner member to cut or resect bodily tissue, the cut tissue being aspirated through the inner member.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Surgical cutting instruments for use in closed surgery—also known as "shavers"—conventionally have a straight, elongated outer tubular member terminating at a distal end having an opening in the end or side wall (or both) to form a cutting port or window and a straight, elongated inner tubular member concentrically disposed in the outer tubular member and having a distal end disposed adjacent the opening in the distal end of the outer tubular member. The distal end of the inner tubular member has a surface or edge for engaging tissue via the opening in the distal end of the outer tubular member and in many cases (but not all) cooperates with the opening to shear, cut or trim tissue. In some cases, such as burrs, the opening in the outer tube merely allows access to the tissue and does not otherwise cooperate with the window. The inner tubular member is rotatably driven about its axis from its proximal end, normally via a handpiece having a small electric motor which is controlled by finger actuated switches on the handpiece, a foot switch or switches on a console supplying power to the handpiece. The distal end of the inner tubular member can have various configurations depending upon the surgical procedure to be performed, and the opening in the distal end of the outer tubular member has a configuration to cooperate with the particular configuration of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as cutting blades or edges. Cut tissue is aspirated through the hollow lumen of the inner tubular member to be collected via a vacuum tube communicating with the handpiece.

The aforementioned elongated surgical cutting instruments have also been produced in angled configurations in which the distal tips of the inner and outer members are aligned and offset or bent at a fixed angle from the proximal ends of the aligned inner and outer members. Examples of such fixed-angle rotary surgical instruments are shown in U.S. Pat. No. 4,646,738 (Trott), assigned to the assignee hereof, and in European Patent Application 0 445 918 (Krause et al). In other respects the operation of these fixed-angle shavers is largely the same as that of the straight shavers described above.

Each of the fixed-angle rotary surgical instruments necessarily has the window in the outer member oriented in a fixed position relative to the offset angle. While various fixed-angle instruments may be manufactured, each with a given offset angle and/or with a given window orientation, each instrument necessarily requires that the window be in a fixed position. It has been found that the window could in some instances be better positioned at an orientation different from that normally produced. Obviously manufacturing numerous fixed-angle outer tubes with windows in varying positions would create tremendous inventory problems for users and manufacturers alike. There is a need for an angled shaver system in which the orientation of the cutting window in the outer tube may be easily varied without the need to carry excessive inventory.

Known fixed-angle shavers are produced with only one offset angle—generally 10° to 15°. There is a need for a variety of offset angles in addition to those which are normally produced. Even if a variety of offset angles were produced the user or manufacturer would need to carry a large inventory for varying surgical indications. There is a need for an angled shaver system in which a variety of offset angles could be incorporated into angled shavers.

It is accordingly an object of this invention to produce a rotary surgical cutting instrument in which the offset angle is variable.

It is an additional object of this invention to produce a rotary surgical shaver in which the offset angle is selectable by a user.

It is also an object of this invention to produce a rotary surgical shaver in which the cutting window at the distal tip of the instrument may be oriented in any direction selected by a user.

It is an additional object of this invention to produce a rotary shaver in which the orientation of the cutting window may be combined with any one of several selected offset angles to produce a unique instrument from a single, base system so that a large inventory of product need not be carried.

It is yet another object of this invention to produce a tool for assisting in the creation of uniquely angled rotary shavers.

It is still another object of this invention to produce a system in which a user may create a unique rotary shaver, angled as desired.

It is still another object of this invention to produce a surgical shaver system in which angled shavers may be created from a minimum number of parts.

It is also an object of this invention to produce a surgical shaver system in which variable angle shavers may be created by users and in which the selected angle will be maintained during normal use of the shaver, although another angle may subsequently be created from the same, previously bent shaver.

SUMMARY OF THE INVENTION

These and other objects of this invention are achieved by the preferred embodiment described herein which is a surgical cutting instrument comprising a longitudinally extending rotatable inner shaft adapted to rotate within a longitudinally extending outer tube. The rotatable inner shaft has a cutting surface adjacent its distal end, this cutting surface being operable in conjunction with a cutting window situated at the distal end of the outer tube to enable tissue adjacent the window to be cut or otherwise operated on. The rotatable inner shaft is provided with a flexible section adjacent its distal end which enables the distal end of the inner shaft to be bent through a desired angle while still enabling the cutting member at the distal end to rotate about the axis of the inner shaft. The outer tube is provided with a bendable section proximal to its distal end which enables its distal end to be bent through a selected angle and to retain that angle while the inner shaft rotates within the outer tube. The outer tube is adapted to be bent in any radial direction relative to its axis so that the window at the distal end of the outer tube may be oriented in any direction. It has been found that the outer tube used in some conventional (i.e. straight) rotary shavers may be bent (within a certain range) by a user even if the tube is not provided with a bendable section proximal to its distal end.

The invention also comprises a tool for enabling a user to shape an angled shaver as desired. The angled shaver is provided in a single, straight configuration with varying distal cutting tips as in conventional rotary shavers. The tool and the variable angle shaver disclosed herein enable a user to create an infinite variety of uniquely angled rotary shavers from a single base system consisting of a straight, bendable outer tube and a flexible inner member.

BRIEF DESCRIPTION OF THE DRAWINGS

FIG. 5 is a front elevation view of a tool for enabling a user to bend the outer tube of FIG. 2 into a selected offset angle.

FIG. 6 is a sectional view of FIG. 5 taken along the lines 6—6.

FIG. 7 is a right end view of FIG. 5.

FIG. 10 is a side elevation view of an alternate embodiment of a tool for enabling a user to bend the tube of FIG. 1 into a selected orientation, the tool being shown in an open position.

FIG. 11 is a top plan view of FIG. 10.

FIG. 12 is a sectional view of FIG. 10 taken along the line 12—12.

DESCRIPTION OF THE PREFERRED EMBODIMENT

Figure 1:
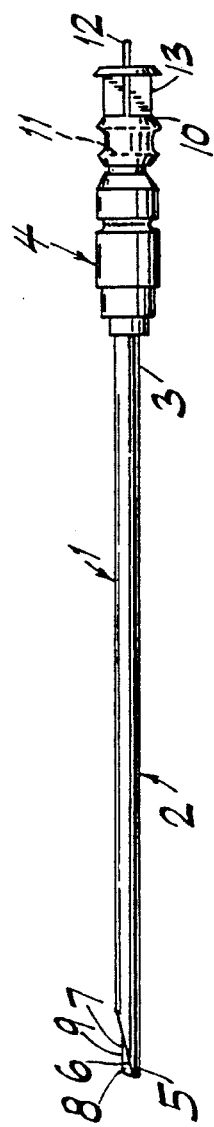
FIG. 1 is a side elevation view of a prior art rotating surgical cutter instrument, more particular described in U.S. Pat. No. 5,061,238, assigned to the assignee hereof and incorporated by reference herein.

A prior art surgical cutting instrument 1 is illustrated in FIG. 1 and includes an elongated tubular outer member 2 made of stainless steel and having a proximal end 3 fixed to a plastic hub 4a and a distal end 5 having an opening 6 therein forming a cutting port or window. An elongated tubular inner member 7 made of stainless steel is rotatably received in outer tubular member 2 and has a proximal end (not shown) fixed to a plastic hub 4b having a configuration to be received in a recess (not shown) in hub 4a and a distal end 8 having a cutting edge 9 formed thereon and positioned adjacent opening 6 such that the cutting edge can engage bodily tissue. The hub of the inner member has a central portion 10 with a transversely extending passage 11 therethrough, the hollow interior of the inner tubular member extending through an axial bore in its hub to communicate with passage 11. A driven tang 12 extends from a portion 13 formed of transverse ribs and is adapted to be driven by a rotating slotted drive shaft of an electric motor in a handpiece.

In the prior art example shown, opening 6 in the distal end of the outer tubular member 2 extends through the side and end walls to produce an edge cooperating with cutting edge 9 formed on distal end 8 of inner tubular member 7 to form a full radius resector. The opening 6 of the prior art device, as well as a comparable opening of the present invention (described below) can have any desired configuration to cooperate with the configuration of the cutting edge or edges on the distal end of the inner tubular member to form a variety of cutting tip designs for various functions.

Figure 2:
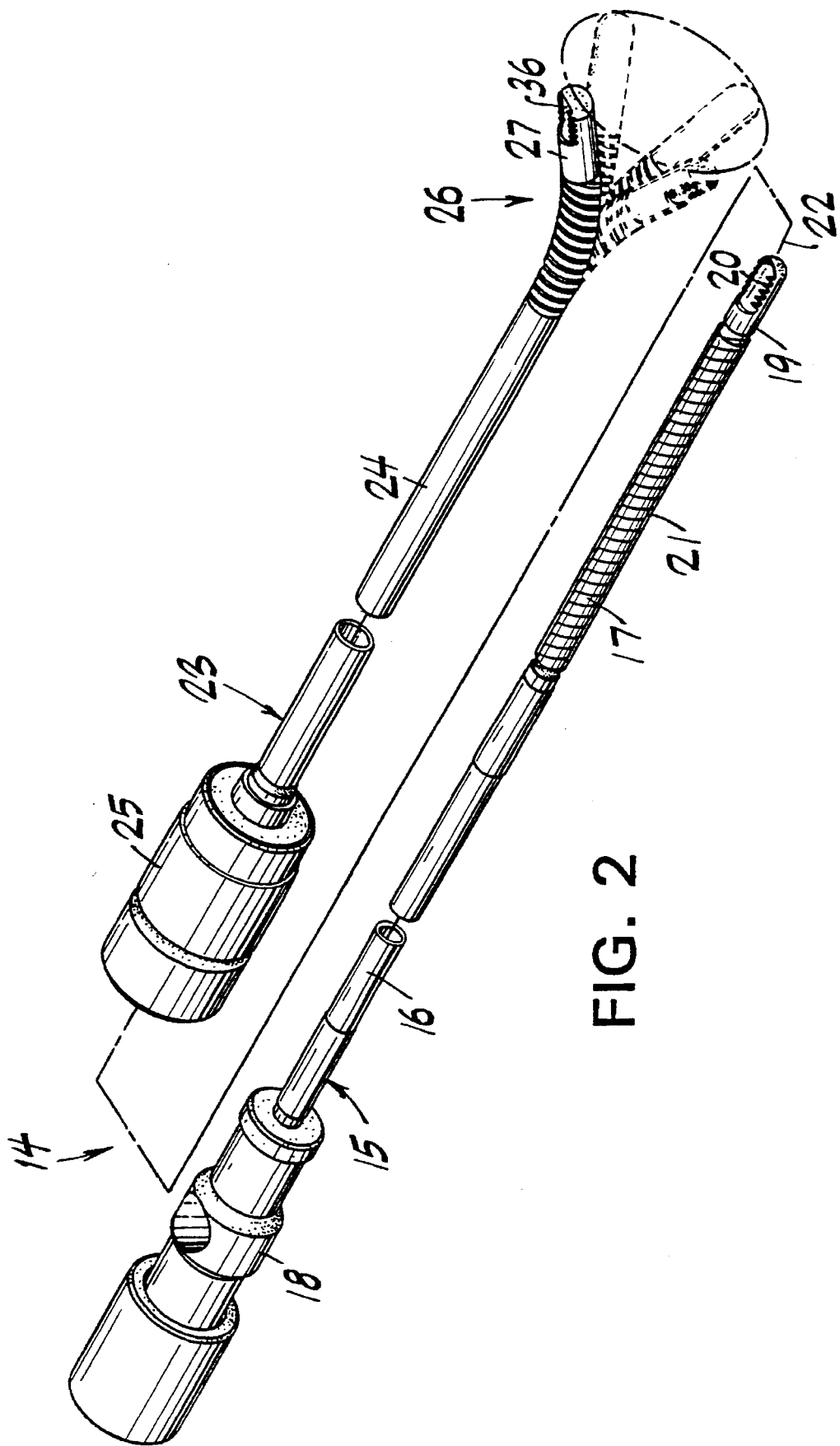
FIG. 2 is an exploded diagrammatic view of a representative inner flexible cutting member and an outer member showing various angular orientations.
Figure 3:
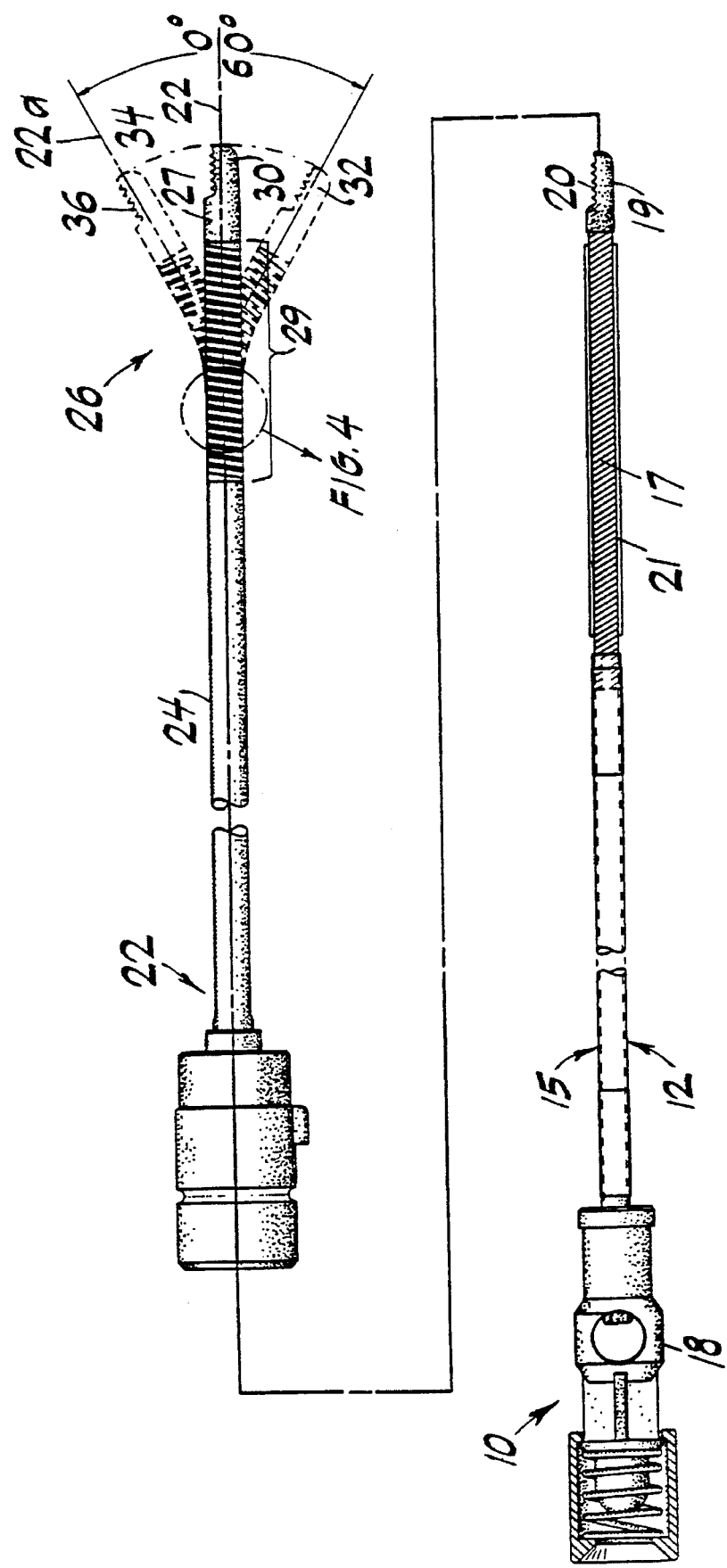
FIG. 3 is a side elevation view of an inner and outer member showing the inner member in cross-section and the outer member in various angular orientations.

Referring now to FIGS. 2 and 3, an exploded view of a surgical cutting instrument 14 is shown and will be referred to herein as a variable angle shaver 14. Both instrument 1 and shaver 14 are to be inserted into a handpiece (not shown) by which the devices are to be powered and manipulated. Shaver 14 comprises a rotatable flexible inner cutting member 15, more particularly described in the aforementioned U.S. Pat. No. 4,646,738 (Trott) which is incorporated herein by reference, and an outer tubular member 23. Members 15 and 23 are analogous in function to members 2 and 7 of the device shown in FIG. 1. Inner member 15 comprises a hollow tube 16 provided with an elongated flexible coupling 17 at its distal end and a plastic hub 18 at its proximal end. Coupling 17 has a cutting member 19 at its distal end which is provided with a cutting edge 20 formed in any one of several selected patterns. The particular embodiment of the inner cutting member shown in FIG. 2 is the subject of a separate co-pending patent application assigned to the assignee hereof and further comprises a flexible bearing sleeve 21 which encases and seals flexible coupling 17. Inner cutting member 15 comprises a plurality of alternately spiraled coiled springs which enable the axis of the distal tip 19 of inner member 15 to be bent relative to the axis 22 of the inner member while still enabling tip 19 to rotate about its axis. While the invention may be produced in a form in which the inner and outer members are assembled prior to bending, a particular advantage of inner member 16 is that it is able to be removed and inserted into a bent outer tube at will.

Figure 4:
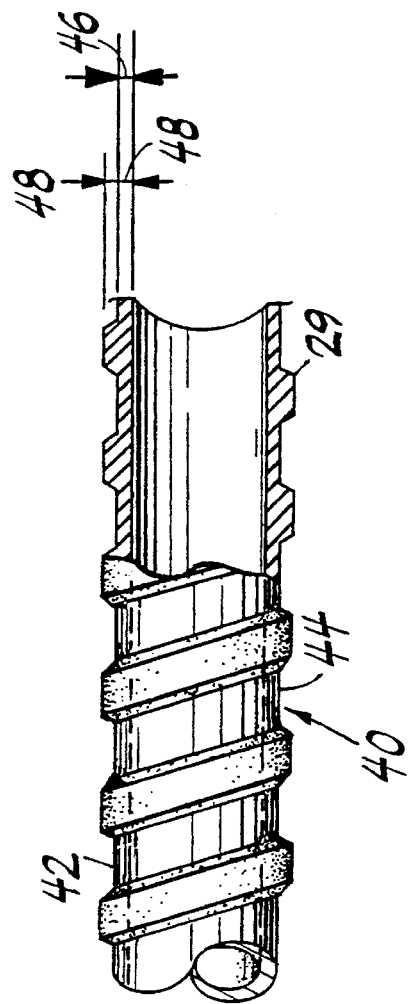
FIG. 4 is an exploded cross-sectional view of a portion of the outer tube shown in FIG. 3.

Outer tubular member 23 is similar in all respects to the prior art outer tube 2 discussed above except that it has an elongated tube 24 attached to a hub 25 and the distal end 26 of tube 24 has a distal tip 27 which may be positioned by a user in a variety of selected angular positions. Distal tip 27 has a window 36 adapted to cooperate with cutting edge 20 of inner member 15. Referring now to FIG. 4, there is shown a close up of section 29 of outer tube 24 which enables the distal tip 27 to be bent by a user into a variety of selected angular positions. Section 29 comprises a spiral relief cut 42 which has a trapezoidal cross-section 44. In the preferred embodiment the overall thickness 48 of tube 24 from the inner surface to the top of the spiral (unrelieved) is 0.013" and the relief cut is formed to a depth such that the root thickness 44 of the outer tube is on the order of 0.008". These parameters have been found to enable the axis 22a of the distal tip 27 of a stainless steel tube 24 to be bent relative to axis 22 to a variety of selected angles between 10° and 25° without any noticeable degradation in performance of the shaver 14.

A variety of outer tube designs could be produced to have bending properties similar to that of tube 24. For example, a tube which is provided with a portion in which some of the material of the tube wall is removed, reduced or somehow relieved of stress on bending would be suitable. Such material-relieved portions could be produced by concentric ring cuts (as opposed to spiral) or by arcuate or longitudinal slots extending through the wall of the tube. A primary requirement of any such alternate embodiment would be that the tube could be bent to a desired degree without unduly reducing the inner diameter of the tube so that rotation of the inner member would not be impaired. If holes in the tube wall are undesirable because the instrument is also used to aspirate fluid from the work site, the material-relieved portion could be encased in a flexible tubular covering which could remain in place before, during and after bending.

Furthermore, as mentioned above, in certain configurations the outer tube may be bent even if it is not provided with any special, stress-relieving portion. The ease and degree of bending are naturally dependent upon the thickness of the outer tube and the material from which it is made. The bending of such conventional, straight outer tubes by a user is considered within the scope of this invention even though the tubes may not be provided with a stress-relieving portion.

Outer tubular member 23 is produced and shipped to a user in a straight configuration 30, as best seen in FIG. 3. This straight configuration is referred to as the "base" from which other, angled configurations may be made. As will be understood below, a user may bend the distal end 26 such that distal tip 27 is put into position 32, position 34 or an infinite number of other positions which cannot be adequately represented in the drawings. In each instance, however, the axis 22a of distal tip 27 is offset obliquely from the axis 22 of the straight, proximal portion of outer tube 24.

It will be understood that window 36 at the distal tip of tube 24 may face toward the direction of the bend as shown in position 34, away from the direction of the bend as shown in position 32 or in any position in between. It will also be understood by reference to FIG. 3 that distal tip 27 may be bent within a plane intersecting straight position 30 and perpendicular to the plane of the page such that window 36 may be oriented in a variety of other orientations relative to the bend. It will be understood by those skilled in the art that an infinite variety of angular orientations may thus be produced from a single base outer tube.

Referring now to FIG. 5, there is shown a front elevation view of tool 60 for enabling a user to bend outer tube 24 in a selected orientation. Tool 60 comprises a mandrel having a plurality of individual stations 62, 64, 66 and 68 providing the user with a template to bend the distal tip 27 of outer tube 24 to a selected offset angle which, in the preferred embodiment, is chosen to be 10°, 15°, 20° or 25° respectively To use tool 60, a user would insert distal tip 27 of tube 24 into a cylindrical bore 62a, 64a, 66a, or 68a, the internal diameter of each bore being chosen to be slightly larger than the outer diameter of distal tip 27. The depth of each bore is sufficient to adequately hold tip 27 as a bend in tube section 29 is created. Each station has extending from it a channel 62c, 64c, 66c or 68c, respectively, each of which is semi-circular in cross-section and adapted to receive an arcuate portion of the outer surface of tube 24. Each one of these channels has a fulcrum portion spaced from the opening of the associated bore and a linear portion of a predetermined length on the side of said fulcrum portion opposite the bore. The linear portion is oriented at an angle relative to the axis of its respective cylindrical bore such that when the distal tip 27 of an outer tube is placed in a cylindrical bore and the tube is bent about the fulcrum portion to lie adjacent the respective channel, the resulting bend created in section 29 will offset the axis 22a of distal tip 27 at an angle substantially equal the number of degrees associated with that particular station. For example, as shown in phantom at station 66, a 20° offset bend may be created in the outer tube 24a by inserting the distal tip 27a of the tube into bore 66a and bending the body of tube 24a about section 29a so that the body of the tube touches channel 66c. Prior to bending, the tube is rotated about its axis to position the window in a desired radial direction. The various angle offsets able to be created by each station are calculated to accommodate a certain degree of spring-back bending allowance depending upon the material of the outer tube. For example, even if an outer tube is bent at a given station to have the body of the tube lie within a respective channel, once pressure is released from the body of the tube it will generally tend to spring back to a position somewhat spaced from the channel and it is this final position which is represented by the offset angle indicia 69 imprinted on the tool.

Figure 8:
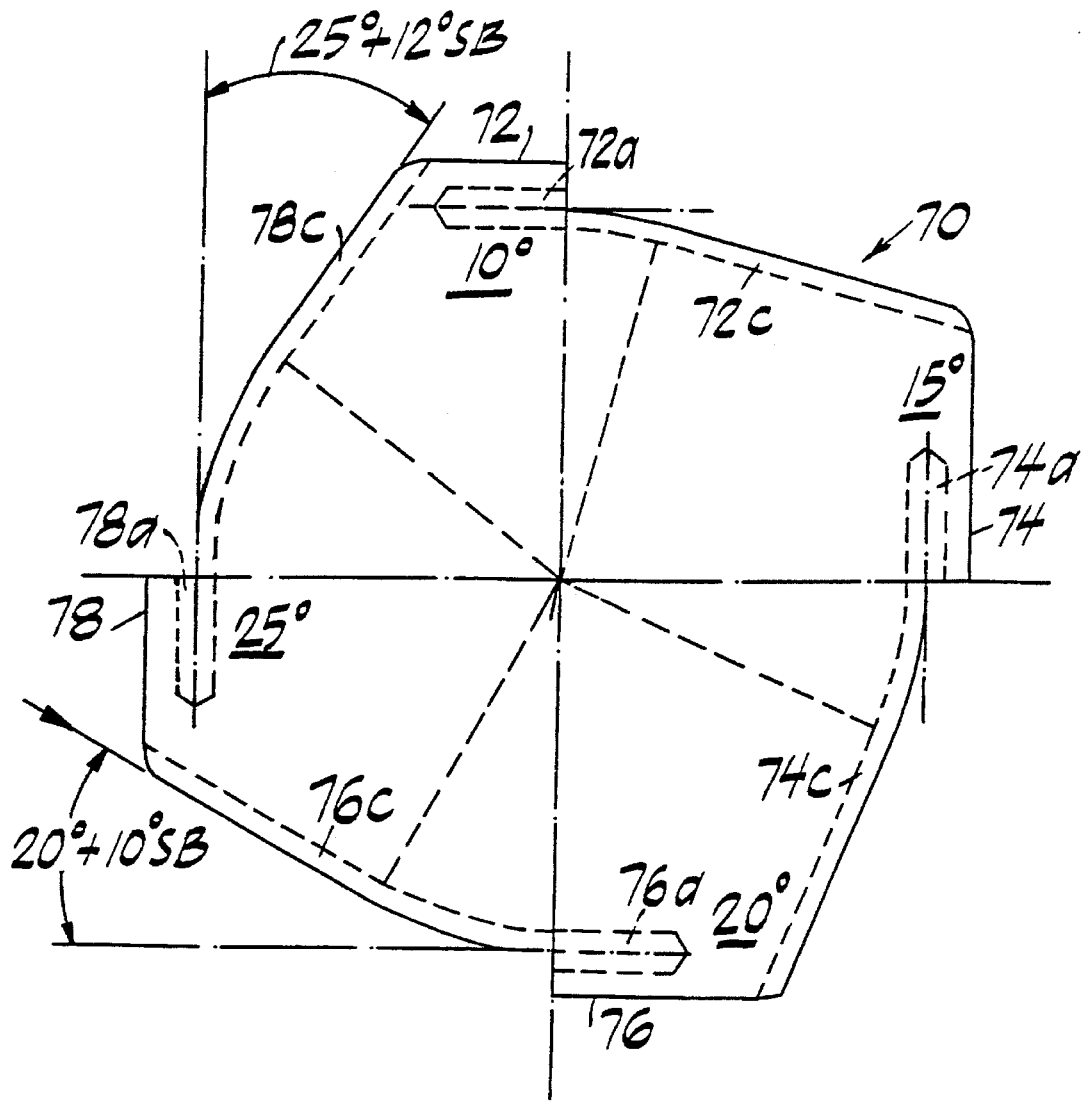
FIG. 8 is a front elevation view of an alternate embodiment of a tool for enabling a user to bend the tube of FIG. 1 into a selected orientation.
Figure 9:
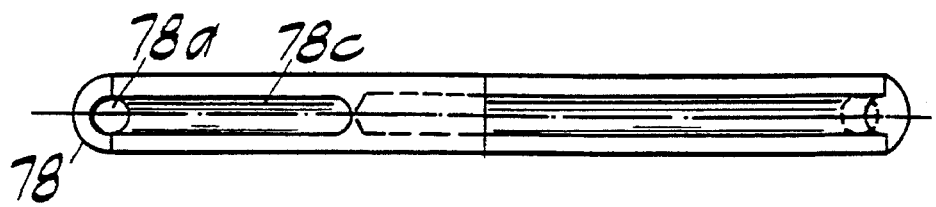
FIG. 9 is a top plan view of FIG. 8.

Referring now to FIGS. 8 and 9, an alternate embodiment of a mandrel tool 70 is shown having a plurality of stations 72, 74, 76 and 78, each being comparable in form and function to the stations 62, 64, 66 and 68, respectively, of tool 60. Each station has a cylindrical bore 72a, 74a, 76a and 78a and an associated semi-circular channel 72c, 74c, 76c and 78c.

Referring now to FIGS. 10 through 13, there is shown an alternate bending tool 80 which is a unique modification of a conventional pipe-bender. Tool 80 comprises a pair of handles 81, 82 pivoted at 83 and having distal ends 84 and 85, respectively. The distal tip of end 84 is provided with a cross-pin 86 adapted to slide within slot 87 of slide block 88 as the handles are squeezed together. The bottom surface of slide block 88 is provided with a semi-circular channel 89 adapted to receive a portion of tube 24 shown in phantom. An aperture 90 (in handle end 85) and a closed-end bore 91 are aligned to receive the distal end of tube 24 and are spaced to provide an opening 92 through which the position of window 36 may be seen.

Figure 13:
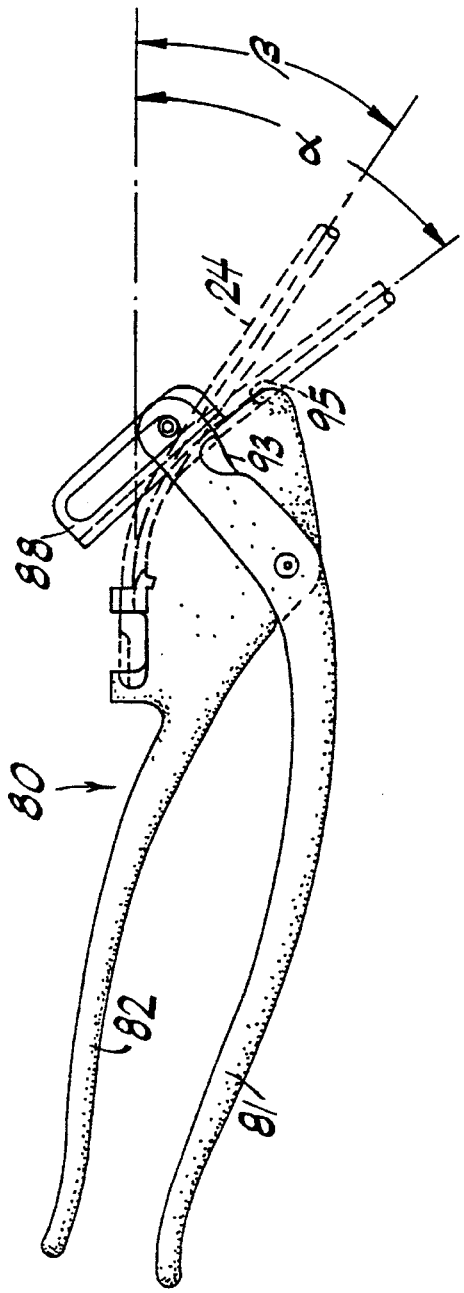
FIG. 13 is a view of FIG. 10 showing the tool in a closed position.

As best seen in FIG. 13, squeezing handles 81 and 82 causes slide block 88 to slide along the outer surface of tube 24 to bend it without abrasion or other actions which may affect the structural integrity of the tube. Index edge 93 is aligned with a selected indicia 94 while the tip of the tube is held in bore 91 in order to create the desired degree of bend. A channel 95 is provided in the distal-facing surface of handle end 85 at an angle with respect to the original straight portion of tube 24 (best seen in FIG. 10) such that when tube 24 is bent to an angle α it will spring back to the desired angle β represented by the selected indicia 94.

Figure 16:
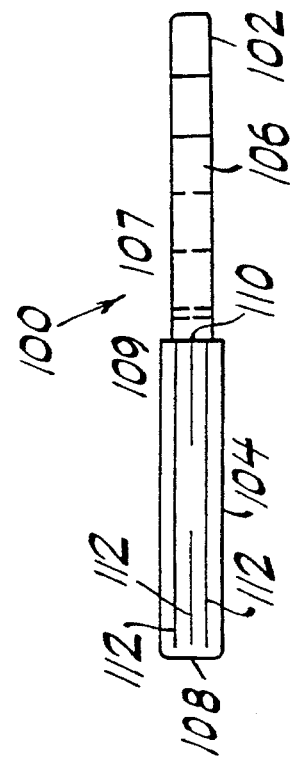
FIG. 16 is a top plan view of the tool shown in FIG. 14.
Figure 15:
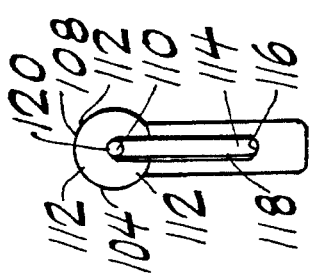
FIG. 15 is a left end view of the tool shown in FIG. 14.
Figure 14:
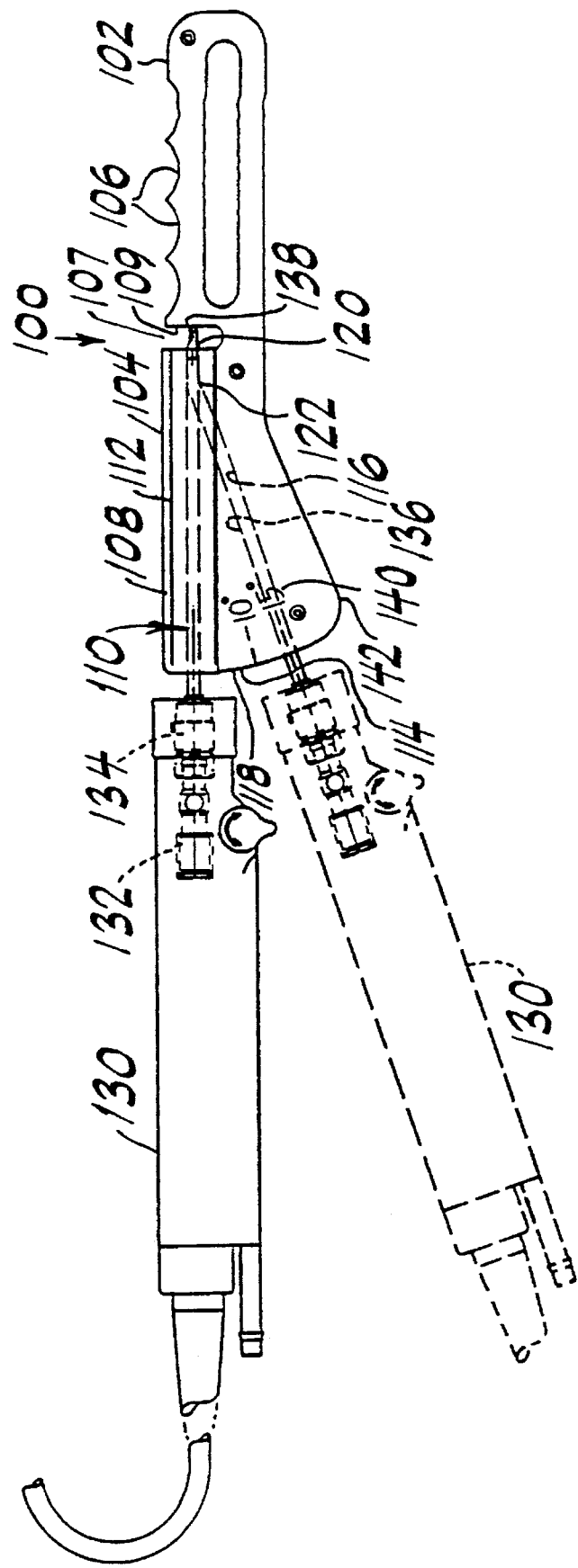
FIG. 14 is a side elevation, diagrammatic view of a rotatable shaver handpiece with the inner and outer elongated members inserted into an alternate embodiment of a bending tool constructed in accordance with the principles of this invention.

FIGS. 14 through 16 show another alternate embodiment 100 of a mandrel tool (not necessarily to scale) having additional, rotational indicia to help a user angularly position the outer tube's distal window relative to the bend to be formed. Mandrel tool 100 comprises a bending portion 104 and a handle portion 102 which includes a plurality of finger recesses 106. Bending portion 104 is spaced from handle portion 102 by an open window area 107 which is large enough to allow easy visualization of the distal window of an outer tube and also prevent any damage to the cutting edges presented at the window. The distal end of window 107 abuts a stop surface 109 which longitudinally positions an outer tube (relative to the below-mentioned fulcrum portion) for proper formation of a bend. Bending portion 104 has an elongated barrel 108 with a central bore 110 and a plurality of circumferentially spaced, longitudinally extending rotational indicia 112. The bottom side of bore 110 communicates with a channel or slot 114 which terminates at an inclined lateral limit surface 116 and the diameter of the bore and width of the slot are sized to receive the outer tube and restrain it from excessive transverse motion. The channel extends longitudinally along tool 100 between an open arcuate proximal end 118 and a circular distal end opening 120 which coincides with bore 110. A fulcrum or anvil portion 122 is interposed on surface 116 between channel ends 118 and 120. A handpiece 130 of a rotatable shaver system is shown in order to demonstrate a method of using tool 100. Handpiece 130 is shown diagrammatically in full lines with an initially straight inner member 132 and outer tube 134 assembled and inserted into bore 110 of tool 100. Handpiece 130 is shown in phantom after outer tube 134 has been bent to an angled configuration 136. Prior to bending, the window 138 of outer tube 134 is oriented as desired relative to rotational indicia 112. Indicia 112 extend the full length of barrel 108 in order to assist the user in aligning the indicia with the distal window 138 as well as with handpiece 130 or with the hub of the outer tube if the handpiece is not used. The barrel is made long enough to enable a user to fully insert an outer tube into bore 110 so window 138 is visible in space 107 (and may be aligned relative to a selected indicia 112) while simultaneously enabling the handpiece or the hub to be aligned with the same indicia.

Separate, lateral indicia 140 are provided to indicate the degree of bend produced in the outer tube. Indicia 140 are labelled in order to account for the characteristic resiliency or spring-back in the outer tube. For example, when the outer tube is aligned with the indicia labelled 15°, the actual bend in the tube is somewhat greater than that (depending on material) but when the bending force is removed the tube will spring back to 15°. The shape of tool 100 facilitates the bending of the outer tube. A user may, for example, hold the tool handle portion 102 in the right hand while holding the handpiece 130 or hub of the outer tube in the left hand. Placing the left thumb on thumb rest portion 142 enables a user to squeeze the left hand to apply sufficient force on the proximal end of the outer tube to gently bend the outer tube to the desired degree, or even with surface 116, without kinking or bending the handpiece out of alignment with the proximal end of the outer tube.

Tool 100 may also have descriptive instructions printed thereon such as the "90° left down/right up" shown in FIG. 14 and the "180° convex" shown in FIG. 16. A user holding the tool and handpiece as shown in FIG. 14 could, by facing window 138 directly towards himself and bending the outer tube to the desired degree, produce an angled shaver having its distal end bending toward the left with the window facing down. By turning the handpiece over 180° the same outer tube becomes one bending toward the right with the window facing up. Similarly, by holding the tool as shown in FIG. 16 and facing the window toward himself and bending the outer tube to a desired degree, the user can produce an angled shaver having a convex curve with the window facing outwardly. While not shown, other descriptive phrases may be included on the opposite side from that shown in FIG. 14 (i.e. "90° Right Down/Left Up") and on the bottom, near surface 142 (i.e. "0° Concave").

Tool 100 is also usable to re-bend an already bent outer tube. A bent tube may be positioned within the channel end openings 118 and 120 and then straightened into alignment with bore 110. Rotating the outer tube about its axis would then help to remove the bend so the outer tube could be repositioned and bent as desired to a new configuration. A limited number of re-bends may be possible, depending on the construction of the rotary shaver inner and outer members.

It will be understood by those skilled in the art that numerous modifications and improvements may be made to the preferred embodiment of the invention disclosed herein without departing from the spirit and scope thereof.

What is claimed is:

1. A tool for facilitating the bending of the outer elongated tube of a rotatable shaver comprising:

a unitary body provided with at least one bending station at which a longitudinally extending tube may be bent;

each said bending station comprising;

a holding portion for holding a selected end of said outer tube against movement in a direction transverse to the axis of the outer tube, said holding portion comprising a channel adapted to accept an end of the outer tube and enabling a user to rotate the outer tube about its axis by rotating the tool itself to enable the bend to be created in any radial direction; and a fulcrum portion spaced a predetermined distance from said holding portion; and a fixing portion situated on the side of said fulcrum portion opposite said holding portion, said fixing portion comprising a surface adapted to contiguously engage said outer tube to enable said outer tube to be bent to a predetermined angle relative to the axis of said holding portion.

2. A tool according to claim 1 wherein said body is planar and said holding, fulcrum and fixing portions are aligned in a common plane.

3. A tool according to claim 1 further comprising a plurality of bending stations, each of which is aligned in a common plane.

4. A tool according to claim 1 further comprising means to limit transverse motion of the portion of the outer tube proximal to the fulcrum, the transverse motion being in a plane normal to the plane in which said outer tube may be bent.

5. A tool according to claim 1 further comprising:

viewing portion for enabling visualization of the distal end of said outer tube.

6. A tool according to claim 1 further comprising longitudinally extending indicia means to rotationally align the distal end of said outer tube relative to the plane in which the tube is bent, said indicia means extending over a substantial length of said outer tube.

7. A tool for facilitating the bending of a tube for use in a rotary surgical cutting instrument, the tube having a window opening at its distal end, comprising:

a pair of handles pivotally joined to each other, one of said handles comprising:
 a tube holding means attached to the distal end of one of said handles;
 means to enable the viewing of the end of a tube to be bent, said viewing means adapted to enable a tube to be rotated to position said window in a desired orientation;
 a fulcrum portion aligned with and distal to said tube holding portion;
 a linear portion aligned with and distal to said fulcrum portion;
and the other of said handles comprising:
 a slide block adapted to pivot about the distal end of said other handle as said handles are squeezed together, said slide block provided with a channel to receive a portion of said tube and adapted to bend said tube about said fulcrum portion and into alignment with said linear portion;
 indicia means to indicate the degree of bend produced in a tube.

8. A tool for bending the outer elongated tube of a rotatable shaver comprising:
an integral body comprising:
 a tube holding portion adapted to hold a selected end of an outer tube against movement in a direction transverse to the axis of said outer tube, said holding portion enabling a user to rotate an outer tube about its axis to enable the bend to be created in any radial direction;
 rotational index means for indicating rotational alignment of said selected end relative to said tube holding portion;
 lateral index means for indicating the angle between a proximal portion of said outer tube and a distal portion thereof;
 an anvil portion spaced a predetermined distance from said holding portion;
 window means for viewing a selected portion of said selected end of said outer tube and for preventing lateral impingement of said selected portion against any surface during the bending of an outer tube in the tool.

9. A tool according to claim 8 wherein said body is planar and said holding, fulcrum and window portions are aligned in a common plane and further comprising a finger support means for assisting in providing leverage during use of the tool.

* * * * *